United States Patent [19]
Hoenig

[11] Patent Number: 6,135,108
[45] Date of Patent: Oct. 24, 2000

[54] APPARATUS ENABLING FLUID FLOW

[75] Inventor: Richard Hoenig, Totowa, N.J.

[73] Assignee: Vital Signs Inc., Totowa, N.J.

[21] Appl. No.: 09/150,405

[22] Filed: Sep. 10, 1998

[51] Int. Cl.[7] ........................................ A62B 9/02
[52] U.S. Cl. ........................ 128/205.24; 128/204.18
[58] Field of Search ....................... 128/201.28, 203.24, 128/205.24, 207.12, 912, 204.18; 138/37, 39, 156, 166; 55/418; 604/266, 268, 9

[56] References Cited

U.S. PATENT DOCUMENTS

| | | | |
|---|---|---|---|
| 3,720,235 | 3/1973 | Schrock | 128/204.18 |
| 3,748,215 | 7/1973 | Lenzi | 138/39 |
| 3,933,171 | 1/1976 | Hay . | |
| 3,942,547 | 3/1976 | Pfitzner | 128/205.24 |
| 4,951,661 | 8/1990 | Sladek | 128/202.27 |
| 5,020,532 | 6/1991 | Mahoney et al. | 128/204.18 |
| 5,065,746 | 11/1991 | Steen | 128/205.24 |
| 5,330,450 | 7/1994 | Lopez | 604/533 |
| 5,458,139 | 10/1995 | Pearl | 128/912 |
| 5,957,894 | 9/1999 | Kerwin et al. | 604/533 |

*Primary Examiner*—Glenn K. Dawson
*Attorney, Agent, or Firm*—R. Gale Rhodes, Jr.

[57] ABSTRACT

Apparatus for preventing blockage or occlusion of a fluid flow path, such as a flow path through which a patient's exhalation gas flows, and/or, which apparatus prevents the fluid flow path from becoming deadheaded.

3 Claims, 5 Drawing Sheets

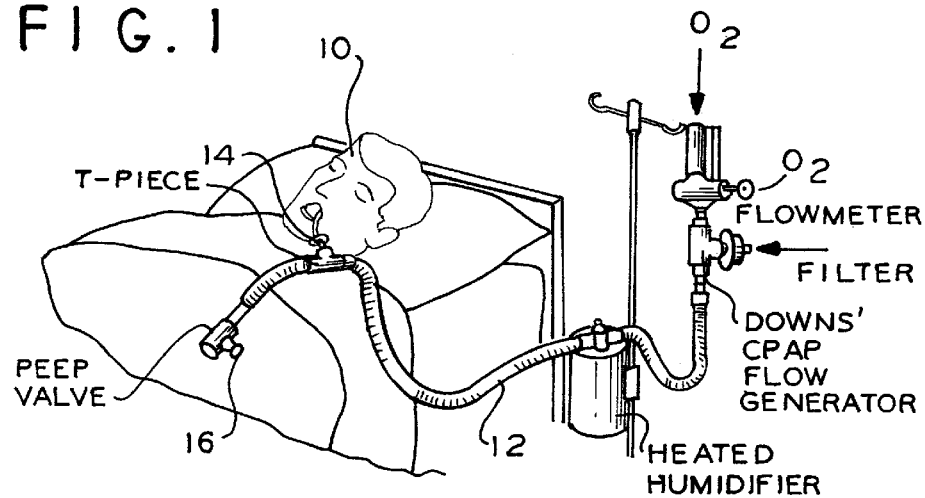
FIG. 1
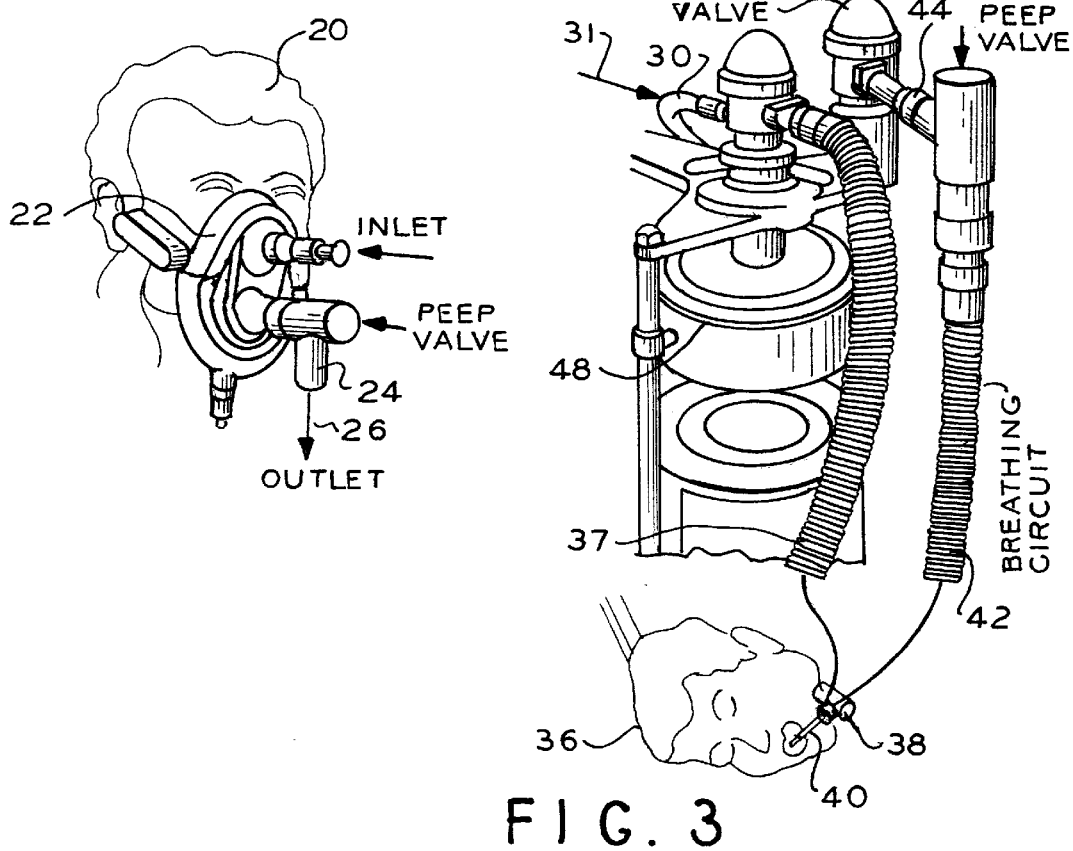
FIG. 2
FIG. 3

APPARATUS ENABLING FLUID FLOW

BACKGROUND OF THE INVENTION

This invention relates generally to apparatus enabling fluid flow and which apparatus includes a surface for providing at least in part a flow path through which a fluid flows and which apparatus is provided with structure for preventing blockage or occlusion of the flow path and for preventing the flow path from becoming blocked downstream or dead-headed. More particularly, this invention relates to a positive end expiratory pressure valve (typically referred to in the art, and hereinafter, as a PEEP valve) which includes a hollow cylinder providing a fluid flow path for exhalation gas from a patient to which the PEEP valve is connected and which hollow cylinder is provided with structure for preventing blockage or occlusion of the fluid flow path and for preventing downstream blockage or deadheading of the fluid flow path.

Numerous apparatus are known to the art which provide a fluid flow path for a fluid such as a gas. Numerous medical apparatus are known to the art which provide fluid flow paths for fluids such as oxygen, anesthesia gas, and the like, and in particular numerous medical apparatus are known to the art which provide a fluid flow path for exhalation gas from a patient's lungs such as air, oxygen, anesthesia gas, or a combination thereof.

A representative medical apparatus known to the art is the above-noted PEEP valve. Such PEEP valves, as known to the art, are used to maintain a predetermined pressure level in the lungs of a patient who is being ventilated with oxygen or anesthetized by a suitable anesthesia gas. Typically, such PEEP valve includes a spring biased relief valve which remains closed and prevents the patient from exhaling until the pressure of the patient's exhalation gas exceeds the setting of the spring biased relief valve after which the valve opens and the patient's exhalation gas is exhausted through, typically, a hollow cylinder provided on the PEEP valve which provides exit port or an internal fluid flow path for the patient's exhalation gas. As the patient is exhaling, the pressure of the exhalation gas falls until it reaches the setting of the spring biased relief valve after which the valve closes thereby preventing the further flow of exhalation gas from the patient's lungs whereupon the gas remaining in the patient's lungs which would be exhaled remains in the patient's lungs and remains in the patient's lungs at a pressure equal to, or at least substantially equal to, the pressure setting of the spring biased relief valve. As is further known to the art, it is advantageous for a patient being ventilated or anesthetized, for example, to have at least some pressure remaining in the patient's lungs and to prevent the patient's lungs from being evacuated during exhalation. The maintenance of such gas pressure in the patient's lungs is believed to have a salutary effect on the sacks or alveoli of the patient's lungs.

Referring to FIG. 1, by way of example, a patient 10 is shown being ventilated by oxygen from a suitable source not shown. oxygen, $O_2$, enters the $O_2$ flowmeter, flows downwardly, and is mixed with air flowing inwardly through the filter and the downward flow of the mixture of oxygen and air is accelerated by the Downs' CPAP Flowmeter shown, which functions in the nature of a Venturi tube, after which the mixture flows through the heated humidifier, through the corrugated tubing 12, through the T-piece, and into the endotracheal tube 14 with which the patient 10 is intubated. When the patient 10 exhales, the exhalation gas from the patient's lungs flows through the endotracheal tube 14, the T-piece, into the PEEP valve through which the patient's exhalation gas exits through an internal fluid flow path provided in the hollow cylinder 16 of the PEEP valve. As is known to the art with respect to PEEP valves, the exit port or fluid flow path can become inadvertently blocked or occluded such as, for example, by a portion of a pillow, sheet or blanket associated with to the patient becoming inserted, or at least partially inserted, into the exit port or fluid flow path provided by the hollow cylinder of the PEEP valve. When this occurs, the fluid flow path through the PEEP valve exit port is blocked or occluded which prevents the patient from completely exhaling causing a build up in the pressure of the gas remaining in the patient's lungs above the set PEEP valve pressure which can result in barotrauma to the patient's lungs or the production of pneumothorax in the patient's lung cavities causing lung injury.

Another example of PEEP valve usage is illustrated in FIG. 2 wherein oxygen or anesthesia gas is administered to the patient 20 through the inlet provided in the mask 22. The PEEP valve shown is mounted to the mask 22 and exhalation gas from the lungs of the patient 20 normally exits through the internal exit port provided in the hollow cylinder 24 of the PEEP valve; the exhalation gas exits through the exit port as indicated by the arrow 26. Similar to the illustration shown in FIG. 1, the exit port, or internal exhalation fluid flow path provided by the hollow cylinder 24, can become blocked or occluded by the inadvertent insertion of a portion of the patient's pillow, sheet, blanket, or other objects or materials into the PEEP valve exit port.

An illustration of downstream blockage, occlusion, or deadheading of the exit port or internal exhalation fluid flow path provided by the hollow cylinder of a PEEP valve is illustrated in FIG. 3. Unlike FIGS. 1 and 2 which illustrate open systems, FIG. 3 illustrates a closed loop system wherein there is a circular flow of gas, such as oxygen to a patient. Fresh inlet gas such as oxygen enters the system through the hose 30 as indicated by the arrow 31 and flows to the patient 36 through the corrugated tubing 37. The gas enters the T-piece 38 and flows through an endotracheal tube 40 with which the patient 36 is intubated and into the patient's lungs, not shown. Exhalation gas from the patient's lungs flows upwardly through the endotracheal tube, the T-piece 38, and the corrugated tubing 42 and through the PEEP valve shown to the expiratory dome valve shown; in particular, the exhalation gas from the patient's lungs flows through the exit port or internal fluid flow path provided by the hollow cylinder 44 of the PEEP valve to the expiratory dome valve. From the expiratory dome valve, the exhalation gas flows through a tube, not shown, into the bottom of the carbon dioxide, $CO_2$ absorber 48 which absorbs $CO_2$ from the patient's exhalation gas and from the absorber 48 the exhalation gas with the carbon dioxide removed is mixed with the fresh inlet gas 3 and is recirculated to the patient 36. As known to those skilled in the art, failure can result in virtually any component of the closed loop system shown in FIG. 3. For example, there could be a failure in the expiratory dome valve, or the absorber 48, and such failure could result in a downstream blockage or occlusion of the circulatory exhalation gas flow described above which could result in a downstream blockage or occlusion of such exhalation gas circulatory flow causing the flow of exhalation gas through the hollow cylinder 44 of the PEEP valve to be blocked which is typically referred to in the art as deadheaded.

Accordingly, there is a need in the art for apparatus which prevents blockage or occlusion of the above-described fluid flow paths and which prevents such fluid flow paths from being deadheaded.

SUMMARY OF THE INVENTION

It is the object of the present invention to satisfy the foregoing needs in the art.

Apparatus satisfying such foregoing needs and embodying the present invention may include apparatus for preventing blockage or occlusion of a fluid flow path, such as a flow path through which a patient's exhalation gas flows, and/or, which apparatus prevents the fluid flow path from becoming deadheaded.

DESCRIPTION OF THE DRAWINGS

FIGS. 1 and 2 are diagrammatical illustrations showing how the internal fluid flow path of the exit port of the PEEP valve can be inadvertently occluded thereby blocking the flow of exhalation gas from a patient's lungs;

FIG. 3 is a diagrammatical illustration of how the fluid flow path of a PEEP valve connected in a closed loop or circulatory system can become deadheaded as a result of a downstream blockage or obstruction of the patient's exhalation gas flow path;

DESCRIPTION OF THE PREFERRED EMBODIMENT

The present invention will be described with regard to a PEEP valve, although it will be understood that such is merely by way of example and that the present invention is not limited to PEEP valves.

Figure 4:
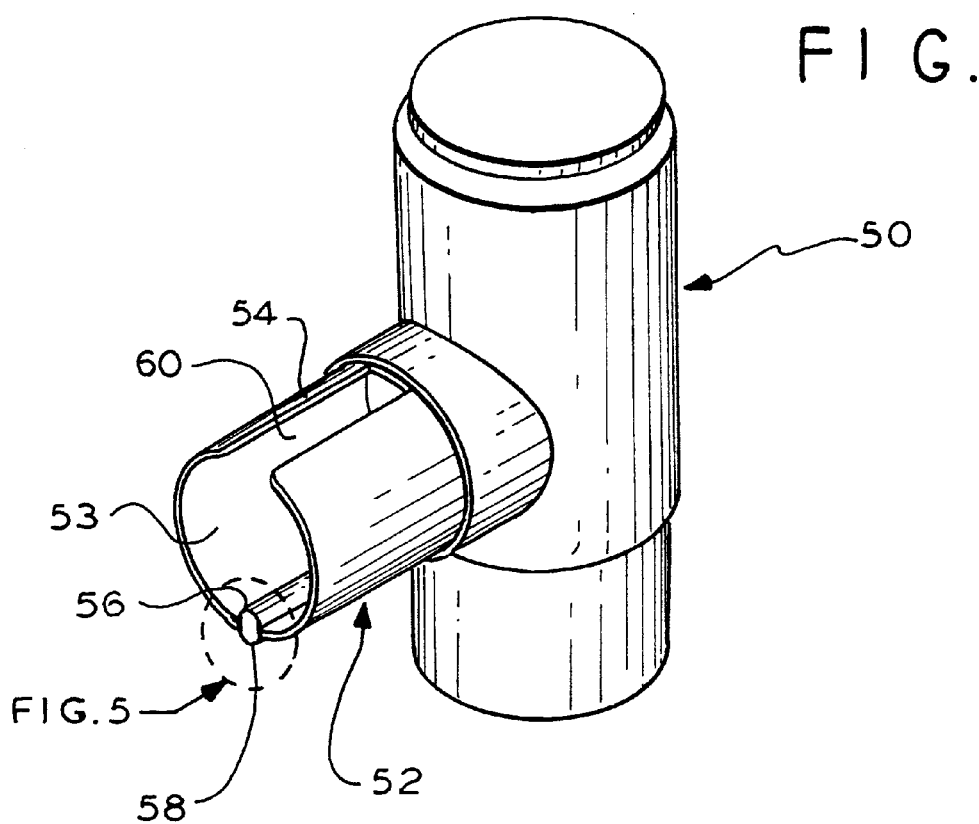
FIG. 4 is a perspective view of a PEEP valve embodying the present invention.
Figure 5:
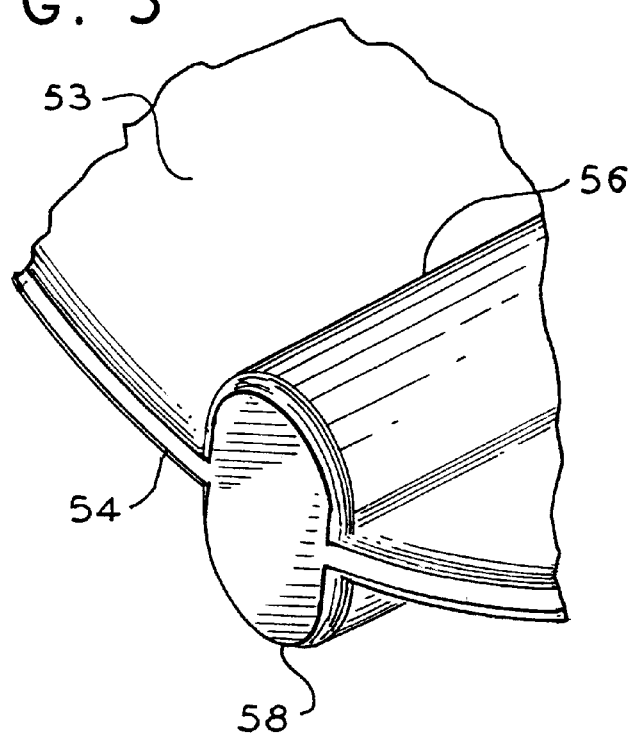
FIG. 5 is an enlarged view of the encircled portion of FIG. 4.

Referring to FIG. 4, a PEEP valve embodying the present invention is shown and indicated by general numerical designation 50. Although not shown, it will be understood that the PEEP valve 50 is provided with an internal valve, or relief valve, such as a spring biased flapper valve, set to open and close at a predetermined pressure, such as for example, between 2.5 and 20 cm H$_2$O. As described above, such valve will not open until the exhalation gas from a patient reaches the valve setting, and such valve will close upon the pressure of exhalation gas dropping to the valve setting thereby maintaining gas in the patient's lungs which would otherwise be exhaled at, or substantially at, the valve setting. The PEEP valve 50 includes a hollow cylinder indicated by general numerical designation 52 which includes an inner cylindrical surface 53 and an outer cylindrical surface 54. The inner cylindrical surface 53 provides an exit port, exhalation port, or internal fluid flow path, through which exhalation gas from a patient flows. A projection 56, note FIGS. 4, 5 and 7, extends inwardly from the inner cylindrical surface 53 into the exit port or fluid flow path provided by the inner cylindrical surface 53 and a projection 58 extends outwardly from the outer cylindrical surface 54 of the hollow cylinder 52; the projections 56 and 58 are best seen in FIG. 5.

Figure 6:
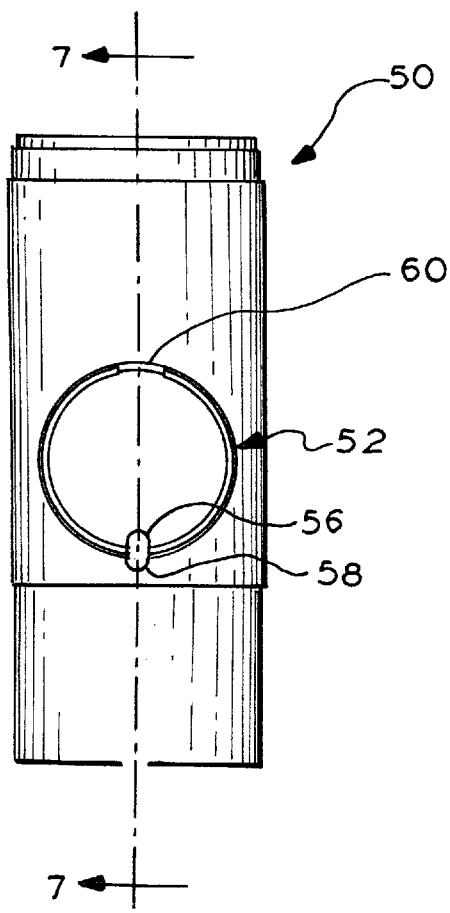
FIG. 6 is a front elevational view of the PEEP valve shown in FIG. 4.
Figure 8:
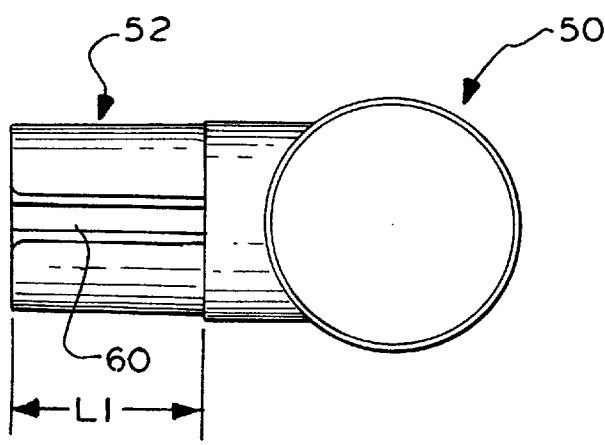
FIG. 8 is a top view of FIG. 7 but shown in closed view.
Figure 7:
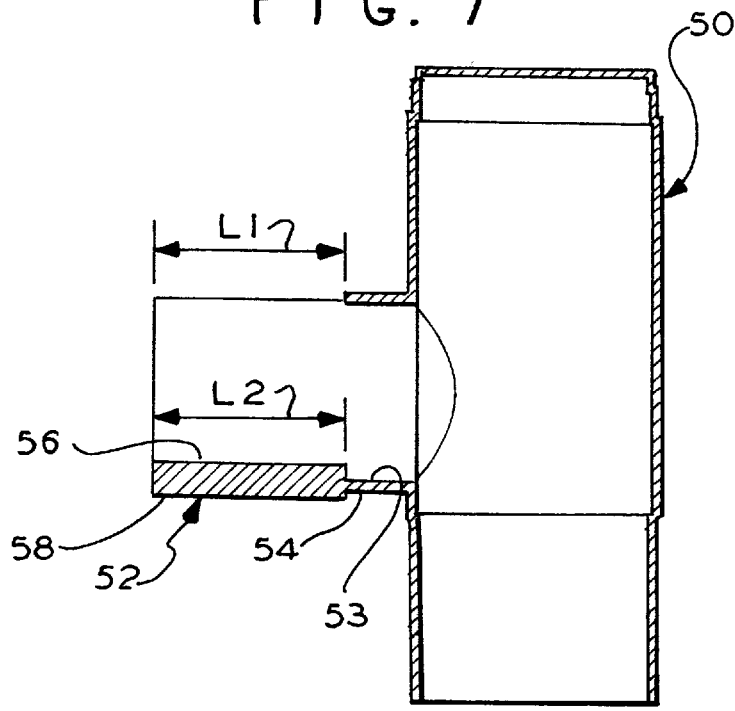
FIG. 7 is a vertical cross-sectional view taken generally along the line 7—7 in FIG. 6.

The top portion of the hollow cylinder 52, as will be best understood from FIGS. 4, 7 and 8, is provided with a longitudinally extending axial slot 60 opening to the end of the hollow cylinder 52. As will be noted from FIG. 8, the hollow cylinder 52 has a length L1 and, as will be noted from FIG. 7, the projections 56 and 58 and slot 60 have a length L2 substantially the same as the length L1. The slot 60 as an axial slot in the sense that it is parallel to the axis of the hollow cylinder 52. From FIG. 6, it will be noted that in the preferred embodiment the projections 56 and 58 and the slot 60 are diametrically aligned.

Figure 9:
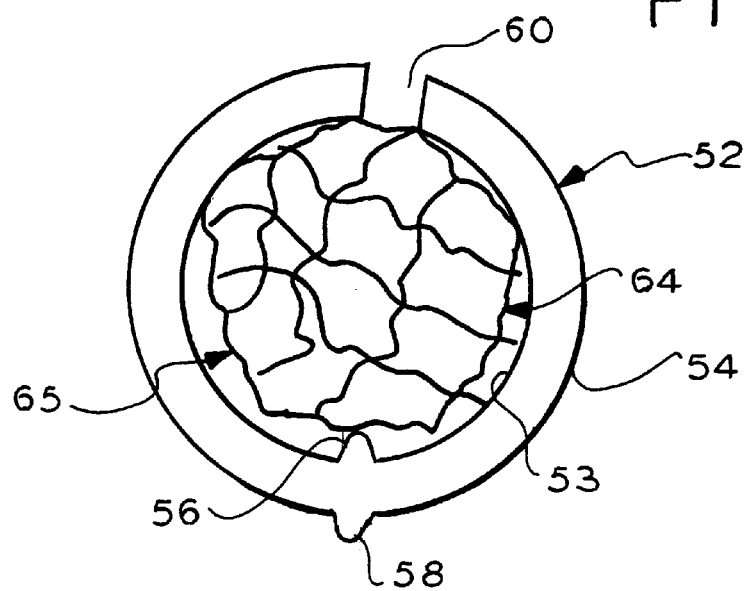
FIGS. 9 and 10 are diagrammatical illustrations illustrating how the present invention prevents the fluid flow path to the hollow cylinder of a PEEP valve from becoming blocked or occluded upon an object being inadvertently inserted into the fluid flow path.
Figure 10:
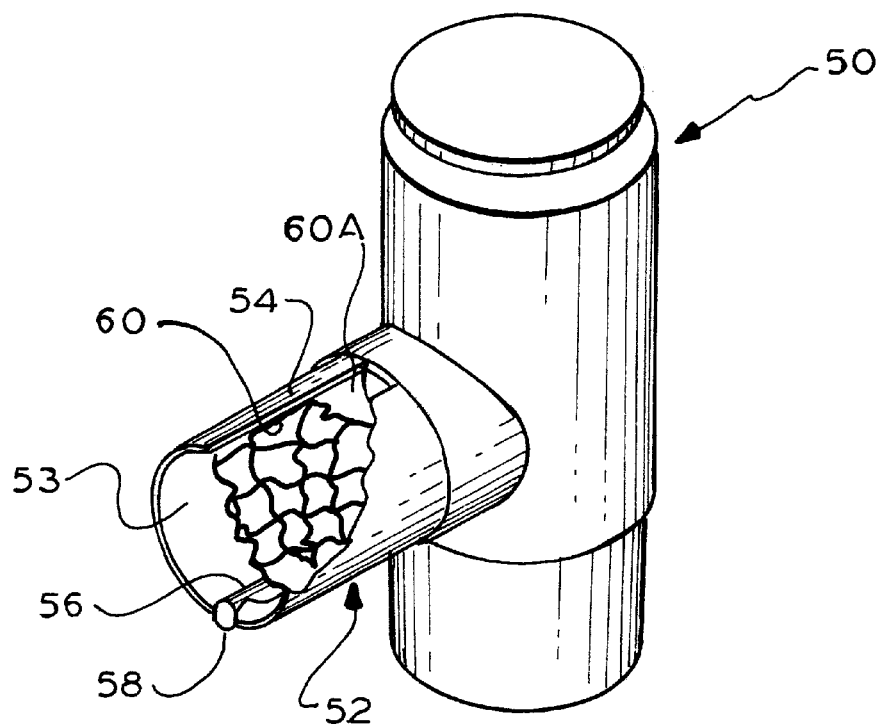

Referring to the diagrammatical illustrations of FIGS. 9 and 10, a representative object, such as for example, a portion of a pillow, sheet, blanket, associated with a patient, is illustrated in FIGS. 9 and 10 by the irregular lines and general numerical designation 64. As illustrated particularly in FIG. 9, upon such object 64 being inserted, or at least partially inserted, into the patient exhalation gas flow path provided by the inner cylindrical surface 53 of the hollow cylinder 52, the projection 56 engages such object and provides space indicated generally by the arrow 65 between the object and the inner cylindrical surface 53 thereby preventing occlusion or blockage, or total occlusion and blockage, of the patient exhalation gas flow path provided by the inner cylindrical surface 53. As will be understood from FIG. 10, the slot 60 provides an opening between the inner cylindrical surface 53 and the ambient or the outer cylindrical surface 54 of the hollow cylinder 52, and exhalation gas from the patient can escape through the opening provided by the slot thereby preventing occlusion or blockage, or total blockage or occlusion, of the patient exhalation gas flow path provided by the inner cylindrical surface 53 of the hollow cylinder 52.

Figure 11:
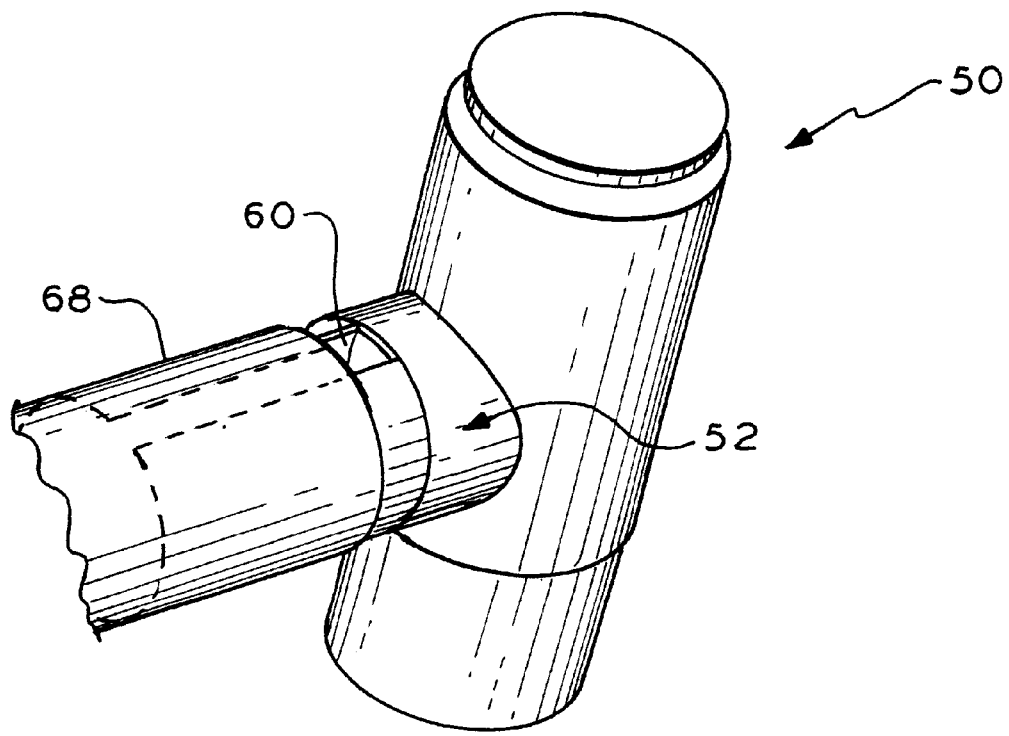
FIGS. 11 and 12 are diagrammatical illustrations illustrating how the present invention prevents deadheading of the fluid flow path of the PEEP valve upon a member such as a cylindrical connector being inserted or forced over the hollow cylinder providing the PEEP valve fluid flow path.
Figure 12:
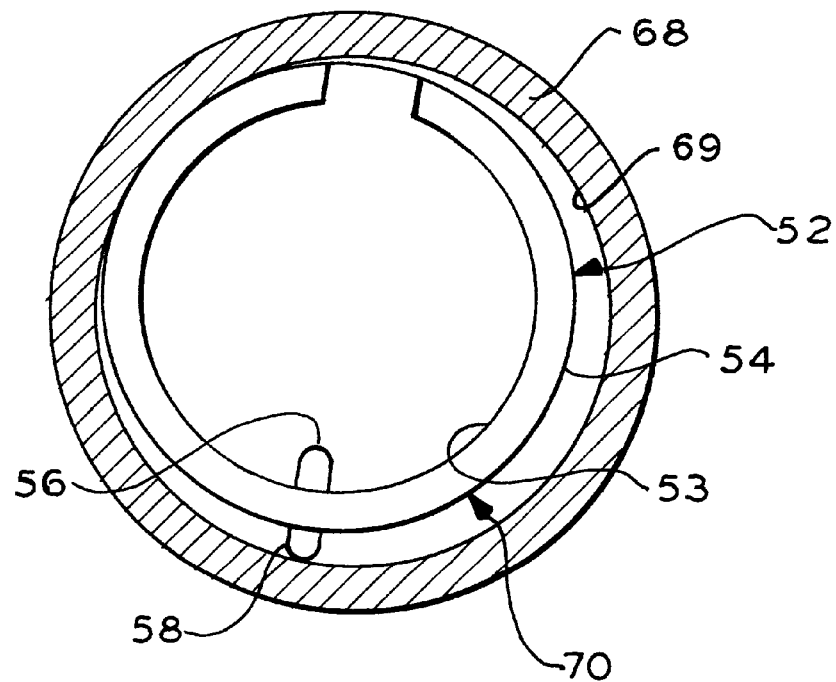

It will be understood that a purpose of the projections 58, extending outwardly from the outer cylindrical surface 54 of a hollow cylinder 52 is to prevent the placement of a hollow cylindrical connector over the hollow cylinder 53 of the PEEP valve 50 so that the PEEP valve will provide an open system for the patient's exhalation gas. However, and by way of example, in the event that a hollow cylindrical connector, such as the connector 68 partially shown in solid outline in FIG. 11 and shown in cross-section in FIG. 12, being forced over the hollow cylinder 52 of the PEEP valve 50, the projection 58 extending outwardly from the outer cylindrical surface 54 of the hollow cylinder 52 engages such hollow cylindrical connector 68 and provides space, indicated generally by the arrow 70, between the inner surface 69 of the hollow cylindrical connector 68 and the outer cylindrical surface 54 of the hollow cylinder 52 and which space 70 provides an escape path for exhalation gas from the patient in the event of a downstream blockage caused by the failure of downstream apparatus connected to the hollow cylindrical connector 68 as described above in connection with the closed loop system illustrated in FIG. 3. Thus the projection 58 prevents the patient's exhalation gas flow path provided by the inner cylindrical surface 53 of the hollow cylinder 52 from becoming deadheaded.

It will be understood that many variations and modifications may be made in the present invention without departing from the spirit and the scope thereof.

What is claimed is:

1. A PEEP valve for maintaining pressurized gas in a patient's lungs, said PEEP valve comprising:

a hollow cylinder including an inner cylindrical surface providing a patient's exhalation gas flow path;

a projection extending inwardly from said inner cylindrical surface and into said flow path and for engaging an object inserted at least partially into said hollow cylinder and for providing space between the object and said inner cylindrical surface to prevent the total occlusion of said flow path by the object;

said hollow cylinder has an axial length and wherein said projection has an axial length substantially equal to said axial length of said hollow cylinder; and said hollow cylinder provided with an axial slot extending laterally through said hollow cylinder and having a length substantially equal to said axial length of said hollow cylinder and said slot for communicating said flow path to the ambient upon the object being at least partially inserted into said hollow cylinder.

2. The apparatus according to claim 1 wherein said projection is a first projection and said hollow cylinder includes an outer cylindrical surface and wherein said apparatus further comprises a second projection extending outwardly from said outer cylindrical surface and for engaging a member placeable over said hollow cylinder to provide space between the member and said outer cylindrical surface to prevent said flow path from being deadheaded.

3. The apparatus according to claim 2 wherein said first projection, said second projection and said axial slot are aligned substantially diametrically.

* * * * *